(12) United States Patent
Harvey et al.

(10) Patent No.: US 10,155,906 B1
(45) Date of Patent: Dec. 18, 2018

(54) FIRE RESISTANT PHOSPHATE CYANATE ESTERS

(71) Applicant: The United States of America as represented by the Secretary of the Navy, Washington, DC (US)

(72) Inventors: Benjamin G. Harvey, Ridgecrest, CA (US); Andrew P. Chafin, Ridgecrest, CA (US); Michael D. Garrison, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/257,525

(22) Filed: Sep. 6, 2016

Related U.S. Application Data

(60) Provisional application No. 62/216,058, filed on Sep. 9, 2015.

(51) Int. Cl.
| | |
|---|---|
| *C09K 21/14* | (2006.01) |
| *C07F 9/12* | (2006.01) |
| *C08G 79/04* | (2006.01) |
| *C08G 79/02* | (2016.01) |

(52) U.S. Cl.
CPC ............ *C09K 21/14* (2013.01); *C07F 9/12* (2013.01); *C08G 79/04* (2013.01)

(58) Field of Classification Search
CPC .................................................. C08G 79/045
USPC ............................................................ 528/399
See application file for complete search history.

(56) References Cited

PUBLICATIONS

Harvey et al ;"Synthesis—phosphate cyanate", Jan. 9, 2015; Royal Society of Chemistry; Chem Abstract 167:420667.*

* cited by examiner

*Primary Examiner* — Duc Truong
(74) *Attorney, Agent, or Firm* — Stuart H. Nissim (57) ABSTRACT

This invention describes resins with phosphate cores and a simple, three-step process for their synthesis. Preferred resins are cyanate ester resins with bridging phosphate groups. These resins can be cured to produce thermoset polymers having $T_g$s of between 131 and >360° C. depending on the number of cyanate ester groups per phosphate and the substitution pattern of the aromatic rings. The high char yields of these resins, up to about 67%, coupled with the phosphate core means that these materials will have applications as fire-resistant polymers. Additionally, these materials can potentially be blended with conventional cyanate esters or other compatible thermosetting resins to improve the fire resistance of composite materials. Other applications may include use in fire-resistant circuit boards, or as surface coatings to reduce flammability of conventional composite materials or thermoplastics.

13 Claims, 6 Drawing Sheets

FIRE RESISTANT PHOSPHATE CYANATE ESTERS

CROSS-REFERENCE TO RELATED APPLICATIONS

This is a non-provisional application claiming the benefit of parent application Ser. No. 62/216,058 filed on Sep. 3, 2015, whereby the entire disclosure of which is incorporated herein by reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

Thermosetting polymer composites offer a variety of advantages over metal structures including lighter weight and resistance to corrosion. Despite these advantages, polymer composites are combustible and this leads to concerns when these materials are used in enclosed environments such as aircraft, surface ships, or submarines. Many high temperature polymers are intrinsically fire resistant. In particular, polymers that contain primarily aromatic groups show excellent fire resistance and high char yields. Incorporating heteroatoms is another way to further increase the fire resistance of high temperature polymers. Most fire resistant additives are based on elements including boron, aluminum, phosphorus, antimony, chlorine, and bromine. Halogenated additives are the most prevalent and act via formation of gas phase radicals that scavenge hydrogen radicals and result in formation of non-flammable HCl or HBr that further dilute flammable oxidants. Although halogenated polymers or additives are effective at reducing flammability, the generation of toxic and corrosive byproducts reduces the attractiveness of these materials. In contrast, phosphorus based flame retardants act through formation of a surface glass that can protect the substrate from oxygen and flame, promote charring, and inhibit free radical propagation. These materials can also act through a vapor phase mechanism in which PO, P, and P2 species react with H and OH radicals to form HPO.

Cyanate ester resins are a well-known class of thermosetting polymers with high intrinsic fire resistance. A number of different approaches have been utilized to decrease the flammability of cyanate esters. One method involves the use of bisphenols that incorporate more rigid aromatic structures. For example, a cyanate ester with a 4,4'-biphenylene structure has been prepared with a char yield of 64% and a UL-94 rating approaching V-0. Another approach is to increase the crosslink density by increasing the number of crosslinking sites per molecule. For example, recently reported tris(cyanate) esters derived from resveratrol resulted in char yields >70% and a heat of combustion of only 2.5 kJ/g. Taking advantage of halogen-based materials, a cyanate ester derived from bisphenol C has been extensively studied. Other researchers have decreased the flammability of cyanate esters by incorporating nitrogen heterocycles. For example, Emrick synthesized a novel triazole containing cyanate ester that was non-flammable and had a heat release capacity of only 10 J/(g·K).

Combining a high temperature thermosetting resin with phosphorus-based flame retardants is another common route to the preparation of fire resistant composite materials. Polyphosphates and diphosphates prepared from bisphenol A have been blended with epoxy resins. Cyanate ester resins containing cyclic phosphinates that can be blended with conventional cyanate esters to generate V-0 grade composites have been prepared. Phosphinated cyanate esters have also been prepared from phenylphosphine oxides, while self-curing phosphine adducts of BADCy and blends with epoxy resins were studied by Lin. Although many of these materials have applications as fire-resistant materials that can be used as standalone resins or blended with conventional materials, there are currently no known examples of cyanate esters with a simple phosphate core.

Cyanate esters with enhanced flame retardancy have applications for electronic and aerospace applications. Several studies have shown that the flame retardancy of cyanate esters can be greatly enhanced through the incorporation of phosphorus. To date this has mostly been accomplished through a blending approach, but there are a few examples of cyanate ester resins that contain phosphate groups covalently bound to the aromatic rings. The current invention describes a simple method for synthesizing bis and tris-cyanate esters that have phosphate groups bridging between the aromatic rings. Through this approach, composite materials with exceptional resistance to fire can be fabricated.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings.

DETAILED DESCRIPTION OF THE EMBODIMENTS OF THE INVENTION

Embodiments of the invention generally relate to phosphate cyanate esters and processes for their synthesis. Ther- mosets made from these phosphate cyanate esters have exceptional char yields and resistance to fire damage.

Incorporating the bridging phosphate groups imparts superior resistance to fire damage. An average P—O bond has a bond dissociation energy about 82 kJ/mol greater than an average P—C bond. The higher average bond dissociation energy of a phosphate translates into greater stability to thermal degradation than related phosphinates. Phosphates are also straightforward precursors to acids and can readily cross-link to form network structures. In addition, the valency of phosphorus readily lends itself to the synthesis of both bis and tris(cyanate) esters. Finally, the increased flexibility of the bridging phosphate group compared to an sp3 hybridized carbon atom results in a high degree of cure.

Phosphate cyanate esters of the present invention comprise the formula:

where $R_1$ is alkyl, aromatic, or and,
where $R_2$ and $R_3$ are

In preferred embodiments, the cyanate group is ortho, meta or para to the phosphate attachment, more preferably meta or para to the phosphate attachment.

In preferred embodiments R is an alkyl of 1-20 carbon atoms, more preferably 1-10 carbon atoms.

In other preferred embodiments R is an aromatic, preferably phenyl or an aromatic ring with additional functionality. An example of a preferred phosphate bis(cyanate) ester comprises the formula:

where R is an alkyl or aromatic, preferably ethyl or phenyl.

An example of a preferred phosphate tris(cyanate) ester comprises the formula:

One preferred synthetic pathway to these phosphate cyanate esters comprises:
  reacting an alkoxy or benzyloxy functionalized phenol with a chlorophosphate in the presence of base to make a phosphate ester
  hydrolysis of ether substituents on the aromatic rings to generate a phosphate-polyphenol; and,
  converting the phosphate-polyphenol to a phosphate-cyanate ester by reaction with a cyanogen halide in the presence of base.

In preferred syntheses, the phenol can be a single or multiple ring alkoxyphenol, bisphenol, or polyphenol, and is allowed to react with a stoichiometric amount of a chlorophosphate. The phenol can have up to 4 additional substituents which can be either alkyl or aromatic. Suitable chlorophosphates include $(RO)PO(Cl)_2$ and $POCl_3$, where R can be any alkyl or aromatic group. Preferred R groups include ethyl and phenyl.

In the case of a single ring alkoxyphenol, one equivalent of a dichlorophosphate is added to a solution containing two equivalents of the phenol in the presence of a base (e.g. triethylamine) to synthesize a bifunctional phosphate. Alternatively, a trifunctional phosphate can be synthesized by reaction of one equivalent of $POCl_3$ with three equivalents of a single ring alkoxyphenol.

Bisphenols can also be used for the reaction, but the rate of addition of the chlorophosphate must be relatively slow. Polyphenols can also be used in the reaction (e.g. dihydroresveratrol), with the degree of functionality dictated by the stoichiometry of the reaction. Mixtures of phenols, i.e. bisphenols and/or polyphenols with monophenols can also be utilized to generate oligomers.

In embodiments where alkoxyphenols are used, the alkoxy group is converted to a phenol. This can be accomplished by a dealkylation reaction using reagents including $BBr_3$, $BCl_3$, pyridinium hydrochloride, aqueous acids or other hydrolyzing reagents. If bisphenols or polyphenols are used, no dealkylation step is required.

In preferred embodiments the alkoxyphenol is a renewable phenol.

In preferred embodiments the starting phenol is multifunctional.

The (poly)phenol phosphate is converted to a multifunctional cyanate ester by, for example, reaction with CNBr, CNCl, cyanogen pseudo halides, or cyanogen sulfonates in the presence of a base.

The phosphate cyanate ester can then be cured on its own, combined with a support material and cured to form a composite, or blended with other cyanate esters, other thermoset resins, or thermoplastics and cured to give a composite material.

One preferred cure reaction is a trimerization of three CN groups to a triazine ring. When the starting material is a monomer with two cyanate groups the resulting trimer structure is a 3D polymer network.

Product properties can be fine-tuned by the choice of substituents in the bisphenolic compound. Bisphenol-A and novolac based cyanate esters are preferred products; bisphenol-F and bisphenol-E may also be used. The aromatic ring of the bisphenol can be substituted with an allylic group for improved toughness of the material. Phosphate cyanate esters can also be mixed with bismaleimides to form BT-resins or with epoxy resins to optimize the end use properties.

In an alternative embodiment, (poly)phenol phosphate can be converted to a variety of different thermoplastics and resins including: polycarbonates, epoxy resins, polyester resins, polysulfones, poly ether ether ketone (PEEK), polyesters, polyester-styrene, alkylphenolics, and polyalylates.

The phosphate cyanate ester can be blended with various support materials including glass fibers, carbon fibers, or other supports and thermally cured (with or without a catalyst) to produce a composite material.

In order to achieve the required properties for a certain application, the phosphate cyanate ester can be blended with conventional cyanate esters to achieve a preferred concentration of phosphates. It can also be blended with thermoplastics or other resins (e.g. epoxy resins) to improve the fire retardancy of those materials.

EXAMPLES

All solvents and chemicals were purchased from Sigma Aldrich and used as received except for triethylamine which was distilled from sodium/benzophenone under nitrogen. NMR spectra were collected with a Bruker Avance II 300 MHz NMR spectrometer. $^1$H and $^{13}$C NMR chemical shifts are reported versus the deuterated solvent peak [Acetone-$d_6$: δ 2.05 ($^1$H), 29.9 ($^{13}$C)]. Elemental analysis was performed by Atlantic Microlabs Inc. Norcross, Ga.

The following examples reference the following synthetic pathways:

Example 1

To synthesize a hybrid resin that combined aromatic cyanate esters bridged by a phosphate group, PO(OEt)Cl$_2$ (ethylchlorophosphate) was allowed to react with two equivalents of p-benzyloxyphenoxide to generate compound 1 (para-) at a yield of 91%. Reductive elimination of the benzyl groups (10% Pd/C/50 psi H$_2$) then yielded bisphenol 3 (para-). Subsequent reaction with cyanogen bromide in the presence of triethylamine generated the bis(cyanate) ester (PhosCy) (para-) in near quantitative yield. PhosCy was stable to column chromatography and was isolated as a thick oil that slowly solidified over time.

The isomer of PhosCy with the cyanate ester group in the position meta to the bridging group (MPhosCy) was prepared by the analogous route through compounds 2 (meta-) and 4 (meta-). MPhosCy was also stable to chromatography and the meta-substitution of the aromatic rings resulted in a liquid resin at room temperature. The low melting points of both PhosCy and MPhosCy make them useful materials for the fabrication of composites.

Example 2 bis(4-(benzyloxy)phenyl) ethyl phosphate (1)(Para-)

To a solution of 4-benzyloxyphenol (10.0 g, 50 mmol) in THF (200 mL) was added 95% NaH (1.26 g, 50 mmol). After the reaction was complete, ethyl dichlorophosphate (3.0 mL, 25 mmol) was added dropwise. The mixture was refluxed overnight then cooled to ambient temperature. 100 mL water was then added. The layers were separated and the aqueous layer was extracted with ether (200 mL). The combined organic layers were dried (MgSO$_4$) and concentrated under reduced pressure to give 11.20 g (91%) of a brown oil.

Example 3

Ethyl bis(4-hydroxyphenyl) phosphate (3)(Para-)

A mixture of the product of the synthesis from Example 2 (11.20 g, 22.8 mmoles) and 10% Pd/C (0.5 g) in methanol (250 mL) was hydrogenated at 50 psi overnight. The solution took up approximately 51 mmol $H_2$. The mixture was filtered through Celite then concentrated under reduced pressure to give 7.14 g (100%) of a yellow oil. The oil was chromatographed on silica gel using 3:1 EtOAc/hexanes to give 5.67 g (85%) of a crystalline solid. $^1$H NMR (acetone-$d_6$): δ 8.38 (s, 2H), 7.07 (dd, J=1.3, 9.1 Hz, 4H), 6.81 (dd, J=0.6, 9.2 Hz, 4H), 4.28 (dq, J=1.5, 7.1 Hz, 2H), 1.31 (dt, J=1.1, 7.1 Hz, 3H). $^{13}$C NMR (Acetone-$d_6$): δ 154.72 (d, J=1.6 Hz), 143.49 (d, J=7.2 Hz), 120.90 (d, J=4.4 Hz), 115.92 (d, J=0.9 Hz), 65.0 (d, J=6.2 Hz), 15.43 (d, J=6.6 Hz).

Example 4 bis(4-cyanatophenyl) ethyl phosphate (PhosCy)

A solution of the product from Example 3 (4.78 g, 16.4 mmol) and cyanogen bromide (3.65 g, 34.5 mmol, 2.1 eq) in THF (100 mL) was cooled to −30° C. and triethylamine (5.0 mL, 36.1 mmoles, 2.2 eq) was then added dropwise. The mixture was allowed to warm to room temperature and stirred for one hour. The mixture was washed with saturated aqueous NaCl then dried and concentrated under reduced pressure to give 5.66 g (96%) of a clear tan liquid. The oil was chromatographed on silica gel using 3:1 EtOAc:hexanes to give 3.88 g (66%) of a colorless oil which slowly crystallizes on standing. mp: 51° C. (DSC). $^1$H NMR (acetone-$d_6$): 7.48 (s, 8H), 4.40 (dq, J=7.1, 8.7 Hz, 2H), 1.36 (dt, J=1.1, 7.1 Hz, 3H). $^{13}$C NMR (acetone-$d_6$): 150.00 (d, J=1.7 Hz), 148.75 (d, J=7.1 Hz), 122.26 (d, J=4.9 Hz), 117.04, 108.44, 66.05 (d, J=6.2 Hz), 15.40 (d, J=6.3 Hz). GC/MS: 360 (M$^+$). Anal. Calcd for $C_{16}H_{13}N_2O_6P$: C, 53.34%; H, 3.64%; N, 7.78%. Found: C, 53.43%; H, 3.54%; N, 7.62%.

Example 5 bis(3-(benzyloxy)phenyl) ethyl phosphate (2)(Meta-)

To a solution of 3-benzyloxyphenol (8.36 g, 41.8 mmol) in THF (150 mL) was added 95% NaH (1.05 g, 41.8 mmoles). After the reaction was complete, ethyl dichlorophosphate (2.5 mL, 20.9 mmoles, 0.5 eq) was added dropwise. The mixture was refluxed overnight and then cooled to ambient temperature. 100 mL water was then added. The layers were separated and the aqueous layer was extracted with 100 mL ether. The combined organic layers were dried (MgSO$_4$) and concentrated under reduced pressure to give 10.06 g (98%) of a thick yellow oil.

Example 6

Ethyl bis(3-hydroxyphenyl) phosphate (4)(Meta-)

A mixture of the product of Example 5 (10.06 g, 20.5 mmol) and 10% Pd/C (0.5 g) in methanol (250 mL) was hydrogenated at 50 psi overnight. The mixture was filtered through Celite and then concentrated under reduced pressure to give 7.62 g (100%) of a clear tan liquid. The oil was chromatographed on silica gel using 1:1 EtOAc:hexanes to give 4.23 g (67%) of a thick colorless oil. $^1$H NMR (acetone-$d_6$): 8.65 (s, 2H), 7.20 (t, J=8.2 Hz, 3H), 6.74 (m, 6H), 4.30 (q, J=7.5 Hz, 2H), 1.33 (t, J=7.5 Hz, 3H). $^{13}$C NMR (acetone-$d_6$): 151.71, 131.87, 128.75, 112.54, 110.84, 107.35, 65.20, 15.40.

Example 7 bis(3-cyanatophenyl) ethyl phosphate (MPhosCy)

A solution of the product of Example 6 (4.23 g, 13.6 mmol) and cyanogen bromide (3.23 g, 30.5 mmoles, 2.2 eq) in THF (100 mL) was cooled to −30° C. and then triethylamine (4.5 mL, 32.3 mmoles, 2.3 eq) was added dropwise. The mixture was allowed to warm to room temperature and stirred for one hour. The mixture was washed with saturated aqueous NaCl then dried and concentrated under reduced pressure to give 4.75 g (100%) of a yellow oil. The oil was chromatographed on silica gel using 1:1 EtOAc:hexanes to give 2.56 g (52%) of a colorless oil. $^1$H NMR (acetone-$d_6$): 7.62 (m, 2H), 7.35 (m, 6H), 4.42 (q, J=7.1, 8.8 Hz, 2H), 1.38 (t, J=1.2, 7.1 Hz, 3H). $^{13}$C NMR (acetone-$d_6$): 153.32, 151.50, 131.92, 118.70, 112.37, 108.16, 107.99, 66.40 (d, J=6.6 Hz), 15.40 (d, J=6.6 Hz). Anal. Calcd for $C_{16}H_{13}N_2O_6P$: C, 53.34%; H, 3.64%; N, 7.78%. Found: C, 53.59%; H, 3.76%; N, 7.64%.

The following examples reference the following synthetic pathways:

Example 8 tris(4-(benzyloxy)phenyl) phosphate (5)

To a solution of 4-(benzyloxy)phenol (10.0 g, 50 mmol) in THF (200 mL) was added 95% NaH (1.26 g, 50 mmoles). When the reaction was complete, trichlorophosphate (1.56 mL, 16.6 mmoles, 0.33 eq) was added dropwise. The mixture was refluxed for four hours then cooled to ambient temperature. Water (200 mL) was then added. The layers were separated and the aqueous layer was extracted with ether (200 mL). The combined organic layers were dried (MgSO$_4$) and concentrated under reduced pressure to give 9.26 g (86%) of an off white solid. This was recrystallized from ethanol (200 mL) to give 8.11 g (76%) of white crystals. mp: 78-79° C. $^1$H NMR (acetone-d$_6$): 7.36 (m, 15H), 7.20 (bd, 6H), 7.02 (bd, 6H), 5.10 (s, 6H). Anal. Calcd for C$_{39}$H$_{33}$O$_7$P: C, 72.66%; H, 5.16%. Found: C, 72.88%; H, 5.15%.

Example 9 tris(4-hydroxyphenyl) phosphate (6)

A mixture of the product of Example 8 (8.02 g, 12.4 mmol) and 10% Pd/C (0.5 g) in 300 mL methanol was hydrogenated at 55 psi overnight. The solution took up approximately 45 mmoles H$_2$. The mixture was then filtered through Celite and concentrated under reduced pressure to give 4.73 g (100%) of a tan glassy solid. This was dissolved in about 30 mL ethanol and poured into 700 mL ice water. The solids were filtered off, washed with water, and then dried to give 4.19 g (90%) of a white solid. $^1$H NMR (acetone-d$_6$): δ 8.43 (s, 3H), 7.08 (dd, J=1.2, 9.0 Hz), 6.84 (dd, J=0.3, 8.7 Hz). $^{13}$C NMR (acetone-d$_6$): 154.91 (d, J=1.7 Hz), 143.37 (d, J=7.8 Hz), 120.95 (d, J=4.7 Hz), 115.99. Anal. Calcd for C$_{18}$H$_{15}$O$_7$P: C, 57.76%; H, 4.04%. Found: C, 57.99%; H, 4.12%.

Example 10 tris(4-cyanatophenyl) phosphate (PhosCy3)

A solution of the product from Example 9 (3.68 g, 9.8 mmol) and cyanogen bromide (3.33 g, 31.5 mmol, 3.2 eq) in THF (200 mL) was cooled to −30° C. and then triethylamine (4.5 mL, 32.4 mmoles, 3.3 eq) was added dropwise. The mixture was allowed to warm to ambient temperature and stirred for one hour. The mixture was washed with brine (100 mL) and the organic layer was separated. The organic fraction was dried (MgSO$_4$) and concentrated under reduced pressure to give 4.08 g (93%) of a white solid. The crude material was recrystallized from EtOAc (150 mL) to give 3.38 g (77%) of white crystals. mp: 123° C. (DSC). $^1$H NMR (acetone-d$_6$): δ 7.37 (bs). $^{13}$C NMR (acetone-d$_6$): 150.17 (d, J=1.6 Hz), 148.14 (d, J=7.0 Hz), 122.04 (d, J=5.0 Hz), 117.10, 108.41. Anal. Calcd for C$_{21}$H$_{12}$N$_3$O$_7$P: C, 56.14%; H, 2.69%; N, 9.35%. Found: C, 56.18%; H, 2.83%; N, 9.25%.

Example 11

X-Ray Crystallographic Analysis

A specimen of PhosCy3 from Example 10, having approximate dimensions 0.192 mm×0.225 mm×0.425 mm, was used for the X-ray crystallographic analysis. A total of 1464 frames were collected. The total exposure time was 8.13 hours. The frames were integrated with the Bruker SAINT software package using a narrow-frame algorithm. The integration of the data using a trigonal unit cell yielded a total of 12418 reflections to a maximum θ angle of 26.37° (0.80 Å resolution), of which 1431 were independent (average redundancy 8.678, completeness=100.1%, Rint=2.33%) and 1378 (96.30%) were greater than 2σ(F2). The final cell constants of a=12.5995(9) Å, b=12.5995(9) Å, c=7.5587(5) Å, volume=1039.16(16) Å$^3$, are based upon the refinement of the XYZ-centroids of 6378 reflections above 20 σ(I) with 5.389°<2θ<54.30°. Data were corrected for absorption effects using the multi-scan method (SADABS). The ratio of minimum to maximum apparent transmission was 0.929. The calculated minimum and maximum transmission coefficients (based on crystal size) are 0.9270 and 0.9660. The final anisotropic full-matrix least-squares refinement on F2 with 113 variables converged at R1=2.55%, for the observed data and wR2=5.91% for all data. The goodness-of-fit was 1.010. The largest peak in the final difference electron density synthesis was 0.147 e−/Å$^3$ and the largest hole was −0.108 e−/Å$^3$ with an RMS deviation of 0.028 e−/Å$^3$. On the basis of the final model, the calculated density was 1.436 g/cm$^3$ and F(000), 460 e−. A CIF file for PhosCy3 has been deposited with the Cambridge Structural Database. The deposition number is CCDC 1406404.

Example 12

Mold Preparation

To prepare cured resin bars for TMA analysis, silicone molds were prepared using Silpak Inc. R2374A silicone mixed with R2374B curing agent in a 10:1 weight ratio. The mixture was degassed for 90 min at ambient temperature under reduced pressure and cured overnight at room temperature followed by 150° C. for 60 min.

Example 13

Preparation of Test Articles from PhosCy and MPhosCy

In separate examples, the cyanate esters of Example 4 and Example 7 were transferred into a mold from Example 12, and placed into an oven at 110° C. under reduced pressure for 30 min to degas. Degassed samples were placed under a nitrogen atmosphere and heated to 150° C. for 3 h and then 210° C. for 24 h. Samples were then cooled to ambient temperature over a 5 h period and removed from the silicone mold. MPhosCy samples were further post-cured at 240° C. for 18 h followed by 3 h at 270° C. Sample bars were 20 mm×2 mm×2 mm in dimension and weighed ~200 mg. Bars were cut to 10 mm in length and were shaved to a height of 2 mm prior to TMA analysis.

Example 14

Preparation of Test Articles from PhosCy3

The cyanate ester crystals from Example 10 were crushed into a fine powder with a mortar and pestle, packed into the mold from Example 12, and placed into an oven at 130° C. under $N_2$. The sample was heated to 180° C. and then placed under reduced pressure for 30 min to degas. The samples were then placed under a nitrogen atmosphere and heated to 230° C. for 24 hr. Samples were cooled to room temperature over a 4 h period and then removed from the silicone mold. Samples were post-cured by slowly heating (over a 60 min period) to 240° C. for 60 min, and then heating to 270° C. for 3 h. Sample bars were 20 mm×2 mm×2 mm in dimension and weighed ~200 mg. Bars were cut to 10 mm in length and were shaved to a height of ~2 mm prior to TMA analysis.

Example 15

Differential Scanning Calorimetry (DSC)

Figure 1:
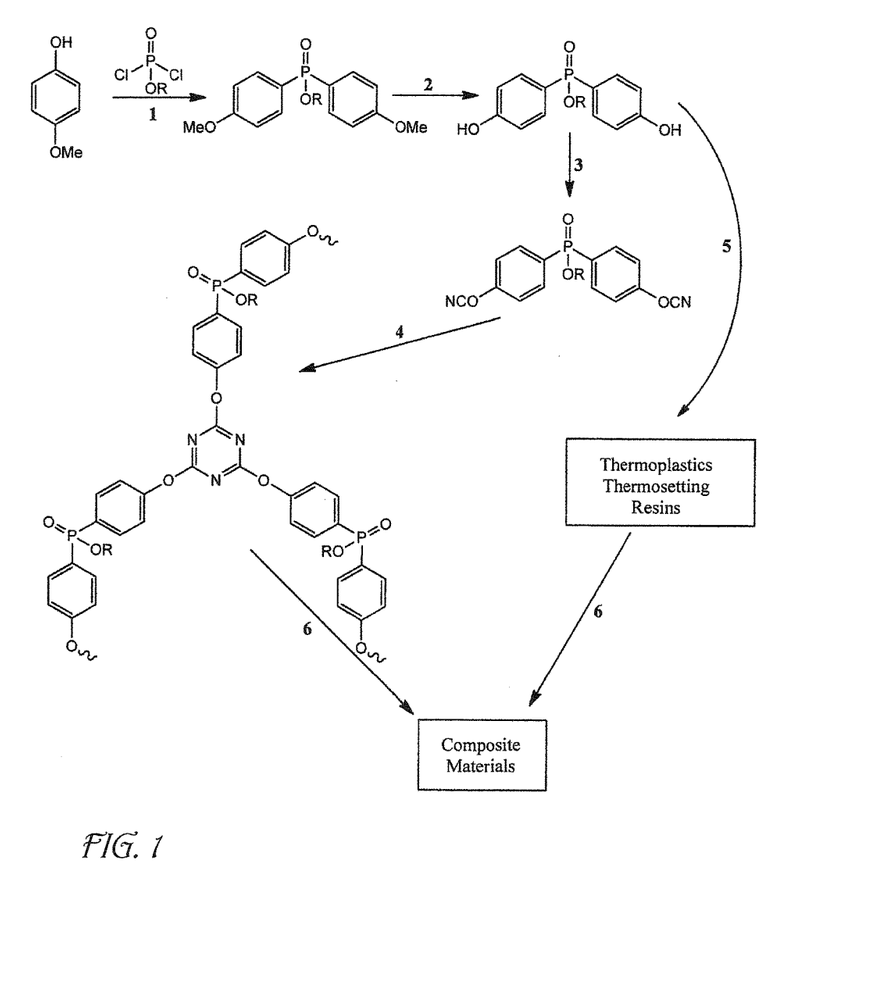
FIG. 1 is an illustration of synthetic schemes for producing cyanate ester resins with bridging phosphate groups according to embodiments of the invention.
Figure 2:
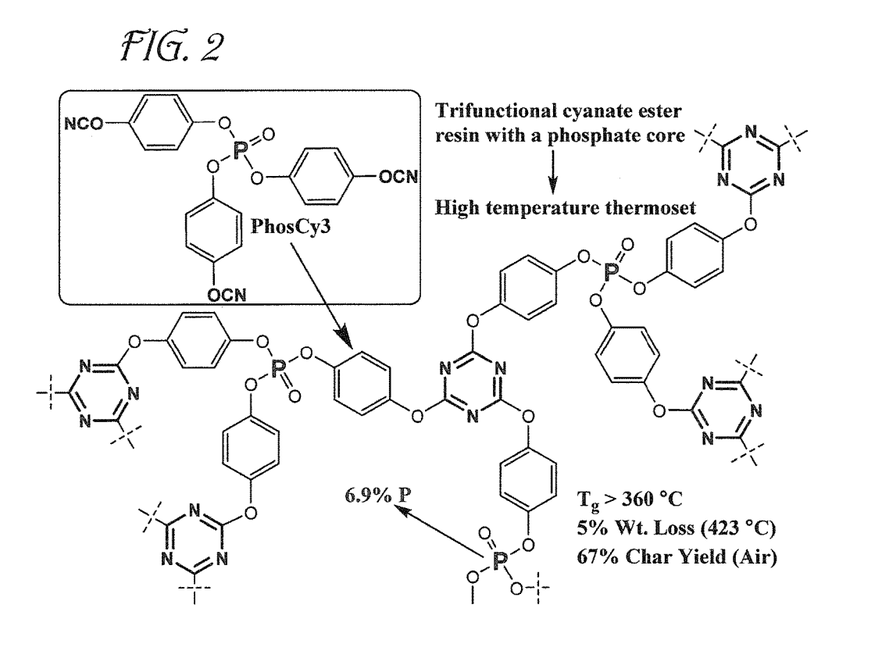
FIG. 2 is an illustration of a trifunctional cyanate ester resin with a phosphate core and its resulting high temperature thermoset according to embodiments of the invention.
Figure 3:
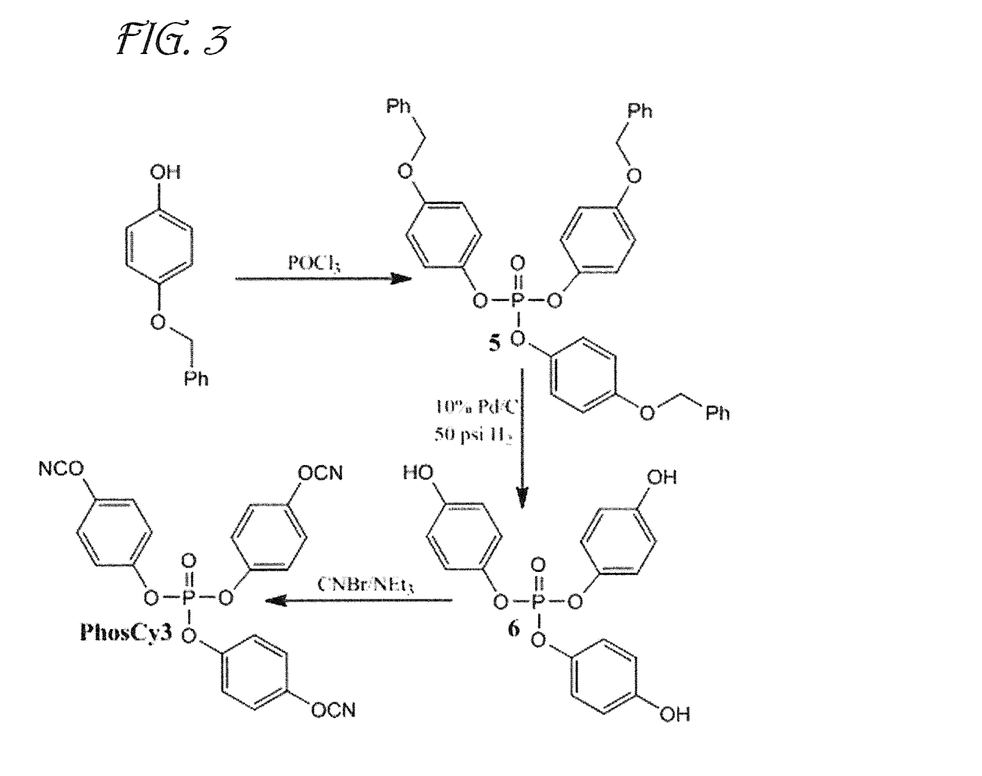
FIG. 3 is an illustration of synthetic schemes for producing tri-cyanate ester resins with bridging phosphate groups according to embodiments of the invention.
Figure 4:
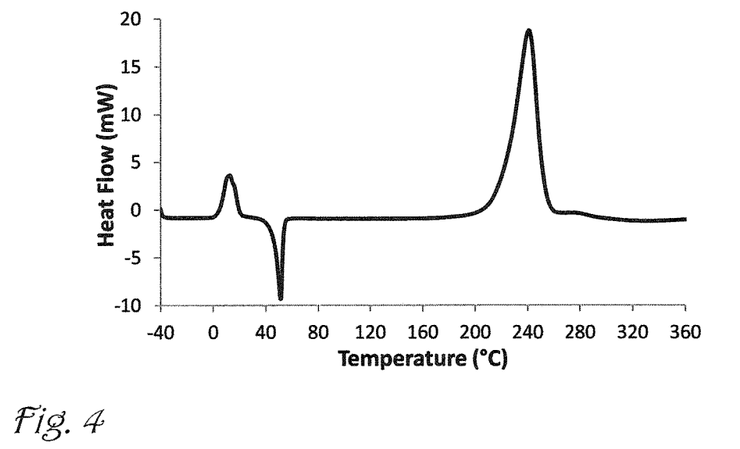
FIG. 4 is a graph showing Differential Scanning calorimetry (DSC) data for PhosCy according to embodiments of the invention.
Figure 5:
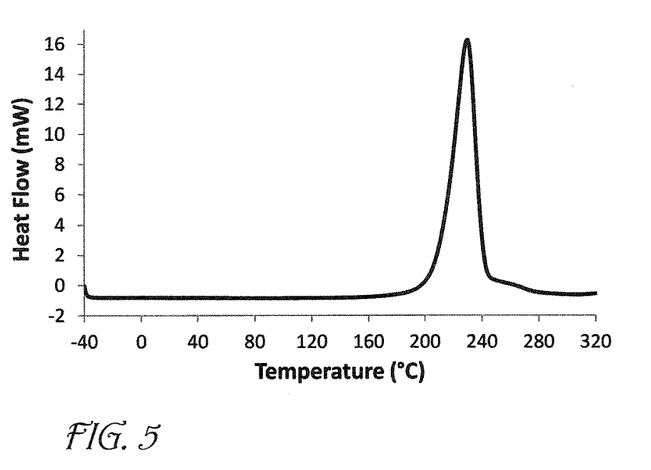
FIG. 5 is a graph showing Differential Scanning calorimetry (DSC) data for MPhosCy according to embodiments of the invention.

The cure chemistry of PhosCy and MPhosCy was probed by DSC. The resulting data is shown in FIGS. 3 and 4, respectively. 5-10 mg pieces of the cyanate ester resins were hermetically sealed in aluminum DSC pans. Samples were then ramped under 50 mL/min of flowing nitrogen at 5° C./min, from −40° C. to 400° C. using a TA Instruments Q100 DSC. The melting points for PhosCy and PhosCy3 were obtained from these experiments and are simply the temperatures corresponding to the maximum endothermic heat flows.

DSC analysis showed that the PhosCy monomer is present as a super-cooled liquid which exhibited a freezing transition at 12.6° C. followed by a sharp melt transition at 51° C. (FIG. 3). The sample was then stable up to ~200° C. at which point the material underwent cyclotrimerization to form a polycyanurate network. The peak of the exotherm was at 241° C. and the change in enthalpy for the trimerization was 110 kJ/(mol —OCN) which is consistent with the typical literature value of 100 kJ/(mol —OCN). MPhosCy showed no low temperature transitions suggesting that it is a permanent liquid at room temperature (FIG. 4). The onset of cyclotrimerization began at a similar temperature compared to PhosCy, with a peak exotherm observed at 230° C. The enthalpy of cyclotrimerization was 105 kJ/(mol equiv. cyanate ester).

The cure chemistry of PhosCy3 was first explored by DSC. The resin melted cleanly at 119° C. The onset of cure for PhosCy3 begins at a lower temperature than for PhosCy or MPhosCy, starting at about 135° C. and continuing up to about 300° C. with a peak exotherm at 248° C.

Despite this, the enthalpy of trimerization was 101 kJ/(mol —OCN), consistent with a high degree of cure.

Example 16

To further examine the cure chemistry of the resins and measure the $T_g$s of the cured thermosets, samples of each resin were thermally cured without addition of a catalyst to generate test articles that were evaluated by FTIR and TMA.

An initial cure cycle of 150° C. for 3 h followed by 210° C. for 24 h was employed for both PhosCy and MPhosCy. To ensure complete cure, the samples were then post-cured at 240° C. for 18 h, followed by 270° C. for 3 h.

Example 17

Dynamic-Mode TMA

Dynamic-mode TMA was performed using a TA Instruments Q400-0537 analyzer under 100 mL/min $N_2$. The bars were placed in contact with a flat, cylindrical probe under a force of 0.10 N. Samples were cooled to −50° C. then heated at 5° C./min to 250-395° C. depending on the sample. The force was modulated ±0.04 N at a frequency of 0.05 Hz during the cycle.

Example 18

Thermogravimetric Analysis Fourier Transform Infrared Spectroscopy (TGA-FTIR)

Samples were analyzed using a Thermo Nicolet Nexus 870 FTIR interfaced via a heated gas cell and transfer line (held at 150° C.) to a TA Instruments Q50 TGA. The TGA was set to ramp from ambient temperature to 600° C. at a rate of 10 degrees per min. FTIR spectra are an average of 32 scans at 4 $cm^{-1}$ resolution. A liquid nitrogen cooled MCTA detector was used. Spectra were background corrected with the gas cell heated and under a nitrogen purge.

Example 19

DFT Calculations

DFT calculations were conducted using Gaussian03 with the basis set 6-31G(d,p) and the B3LYP functional. All compounds were first fully optimized and then a frequency calculation was performed to obtain total energies.

TMA showed that the post-cure actually decreased the $T_g$ of the PhosCy derived thermoset material, but improved the $T_g$ of cured MPhosCy. On this basis, test articles prepared from PhosCy were only cured under the low temperature protocol, while test articles prepared from MPhosCy underwent the high temperature post-cure. FTIR spectra taken before and after the respective heating cycles confirmed that both resins cured completely. TMA revealed a $T_g$ (tan δ) of 223° C. for PhosCy (low temperature cure). In contrast, MPhosCy with its meta-substitution exhibited a maximal $T_g$ (high temperature post-cure) of only 131° C.

Figure 6:
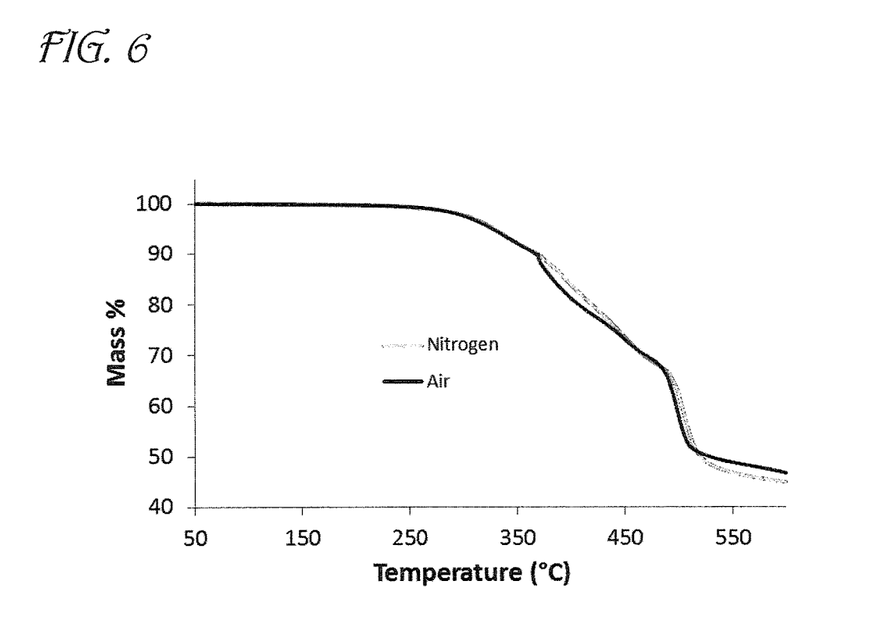
FIG. 6 is a graph showing Thermogravimetric Analysis (TGA) data for PhosCy according to embodiments of the invention.
Figure 7:
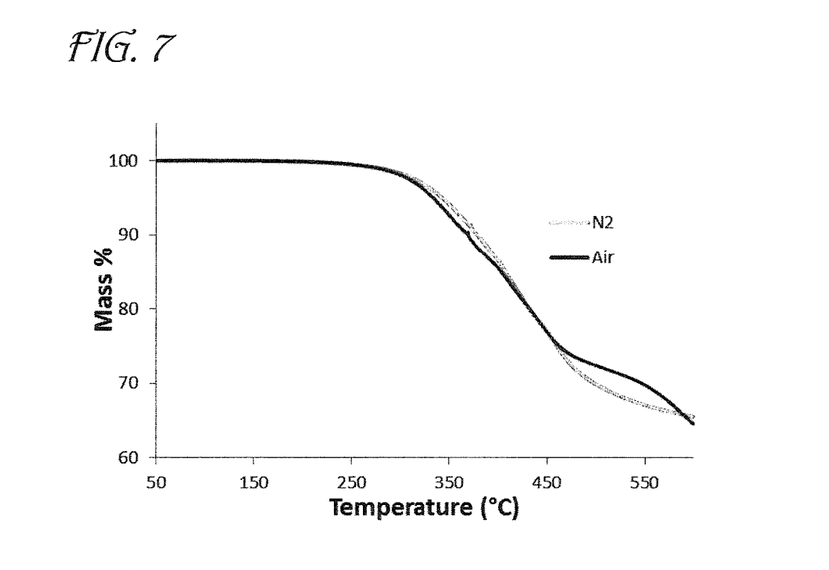
FIG. 7 is a graph showing Thermogravimetric Analysis (TGA) data for MPhosCy according to embodiments of the invention.

The thermal stability and thermal decomposition pathways of PhosCy and MPhosCy were then probed by TGA-FTIR. Under $N_2$, PhosCy lost 5% of its mass at 328° C. and 10% by 368° C. The char yield at 600° C. was 45% under $N_2$ and 47% in air (FIG. 6). MPhosCy showed slightly higher thermal stability with 5% mass loss by 343° C. and 10% mass loss by 379° C. The char yield at 600° C. was an impressive 66% in $N_2$ and 65% in air (FIG. 7).

Cross-linking between phosphate groups at elevated temperature is an important char forming mechanism for phosphate containing polymers. Both the TMA and TGA results suggest that thermal curing of MPhosCy results in end-capped structures that then cross-link through loss of the ethoxy group.

X-ray crystallographic information shows that PhosCy3 has a trigonal pyramidal structure. In the solid state PhosCy3 is chiral and has C3 symmetry. A cured resin bar was prepared under conditions similar to those utilized for MPhosCy and FTIR confirmed that complete cure had taken place. A cured bar was then subjected to TMA. The loss peak and tan δ peaks were still increasing even at 390° C., while the storage trace suggested a $T_g$ of >360° C. This is a remarkable $T_g$ for a cyanate ester, nearly 90° C. higher than BADCy.

Figure 8:
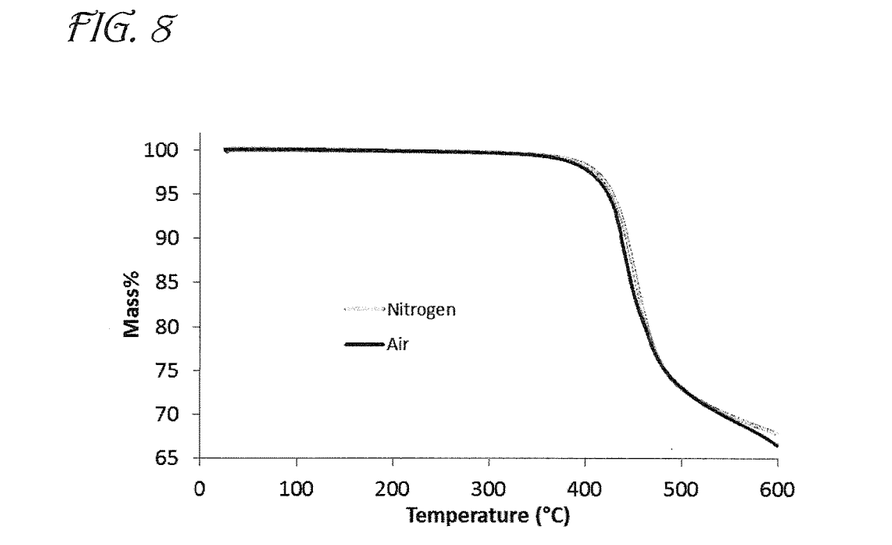
FIG. 8 is a graph showing Thermogravimetric Analysis (TGA) data for PhosCy3 according to embodiments of the invention.

PhosCy3 showed significantly higher thermal stability compared to PhosCy and MPhosCy. TGA/FTIR analysis showed 5% weight loss at 428° C., while 10% weight loss was observed at 443° C. The thermal stability in air was remarkably similar with 5% weight loss at 423° C. and 10% weight loss at 437° C. (FIG. 8). At 600° C. PhosCy3 exhibited a remarkable char yield of 68% in nitrogen and 67% in air.

The key properties of three phosphate cyanate esters are compared in Table 2.

TABLE 2

Key properties of cured phosphate cyanate esters

| Resin | $T_g$ (° C.) | $T_m$ (° C.) | Char Yield ($N_2$) | Char Yield (air) | $\Delta H_{cure}$ (kJ/mol) | % P |
|---|---|---|---|---|---|---|
| PhosCy | 223 | 51 | 45% | 47% | 110 | 8.5 |
| MPhosCy | 131 | <RT | 66% | 65% | 105 | 8.5 |
| PhosCy3 | >360 | 119 | 68% | 67% | 100 | 6.9 |

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

The invention claimed is:

1. A phosphate-bridged compound having the formula:

where $R_1$ is an alkyl group, aromatic group, or and, where $R_2$ and $R_3$ are each or where $R_1$, $R_2$, and $R_3$ can each have up to four additional substituents independently selected from an alkyl or an aromatic group.

2. The phosphate-bridged compound of claim 1 wherein $R_1$, $R_2$, and $R_3$ are:

and each of $R_1$, $R_2$, and $R_3$ having the cyanate ester in the same ortho, meta or para position to the phosphate group.

3. The phosphate-bridged compound of claim 1 wherein $R_1$ is an alkyl group having from 1 to 10 carbon atoms.

4. The phosphate-bridged compound of claim 1 where:
$R_1$ is alkyl, aromatic, and,
$R_2$ and $R_3$ are each,

5. A fire resistant polymeric compound which is the product of the thermal curing of a resin having the formula:

where $R_1$ is an alkyl group, aromatic group, or and,
 where R₂ and R₃ are or .

6. The fire resistant polymeric compound of claim 5 wherein R₁ is

.

7. The fire resistant polymeric compound of claim 5 wherein R₁ is ethyl.

8. The fire resistant polymeric compound of claim 5 wherein R₁ is phenyl.

9. The fire resistant polymeric compound of claim 5 having a char yield in air of at least about 47%.

10. The fire resistant polymeric compound of claim 5 having a char yield in air of at least about 67%.

11. The fire resistant polymeric compound of claim 5 having a glass transition temperature of at least about 131° C.

12. The fire resistant polymeric compound of claim 5 having a glass transition temperature of at least about 360° C.

13. The fire resistant polymeric compound of claim 5 wherein the polymeric compound is a phthalonitrile, benzoxazine, polycarbonate, epoxy resin, polyester resin, polysulfone, poly ether ether ketone (PEEK), polyester, polyester-styrene, alkylphenolic, or polyalylate.

* * * * *